(12) United States Patent
Thorwart et al.

(10) Patent No.: US 6,503,934 B2
(45) Date of Patent: *Jan. 7, 2003

(54) SUBSTITUTED THIADIAZOLESULFONAMIDES

(75) Inventors: Werner Thorwart, Hochheim (DE); Klaus-Ulrich Weithmann, Hofheim (DE); Swen Hölder, Frankfurt am Main (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/779,823

(22) Filed: Feb. 9, 2001

(65) Prior Publication Data

US 2001/0039350 A1 Nov. 8, 2001

Related U.S. Application Data

(62) Division of application No. 09/418,026, filed on Oct. 14, 1999, now Pat. No. 6,218,412.

(30) Foreign Application Priority Data

Oct. 16, 1998 (DE) .......................................... 198 47 823

(51) Int. Cl.⁷ ....................... C07D 285/08; A61K 31/41
(52) U.S. Cl. ....................... 514/361; 544/134; 544/367; 546/209; 548/129
(58) Field of Search ....................... 548/129; 514/361; 544/134, 367; 546/209

(56) References Cited

U.S. PATENT DOCUMENTS

| | | |
|---|---|---|
| 4,758,578 A | 7/1988 | Tegeler et al. |
| 4,873,239 A | 10/1989 | Tegeler et al. |
| 4,985,450 A | 1/1991 | Tegeler et al. |
| 5,556,870 A | 9/1996 | Weithmann et al. |

OTHER PUBLICATIONS

Katherine Tiku et al., "Interleukin 1 Production by Human Polymorphonuclear Neutrophils," The Journal of Immunology, vol. 136, No. 10, pp. 3677–3685 (1986).

N.M. Yousif et al., "Synthesis and Reactions of Some 1,2,4–Thiadiazole Derivatives for Biological Evaluation," Egypt J. Chem., vol. 32, No. 5, pp. 607–614 (1989).

Kelvin Cooper et al., "Chapter 22. Cytokine Modulation as a Medicinal Chemistry Target," Annual Reports in Medicinal Chemistry, vol. 27, pp. 209–218 (1992).

Primary Examiner—Robert Gerstl
(74) Attorney, Agent, or Firm—Finnegan, Henderson, Farabow, Garrett and Dunner, L.L.P.

(57) ABSTRACT

Compounds of the formula (I):

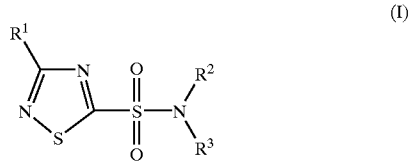

are suitable for the preparation of pharmaceuticals for prophylaxis and treatment of all those diseases where an increased concentration of interleukin-1β participates in their course, for example septic shock, leukemia, hepatitis, muscular degeneration, HIV infections or degenerative joint diseases (such as osteoarthrosis, spondylosis, chondrolysis following joint trauma or prolonged immobilization of joints following meniscus or patella injuries, or torn ligaments), diseases of the connective tissue (such as collagenosis, periodontal diseases, or wound-healing disturbances), and chronic diseases of the locomotor system (such as inflammatory or immunologically or metabolism-related acute and chronic arthritis, arthropathies, rheumatoid arthritis, myalgias and disturbances in bone metabolism).

10 Claims, No Drawings

SUBSTITUTED THIADIAZOLESULFONAMIDES

This is a division of application Ser. No. 09/418,026, filed Oct. 14, 1999, now U.S. Pat. No. 6,218,412 which is incorporated herein by reference.

Under the provisions of Section 119 of 35 U.S.C., Applicants hereby claim the benefit of the filing date of German Patent Application Number 19847823.2, filed Oct. 16, 1998, which Application is hereby incorporated by reference.

FIELD OF THE INVENTION

The invention relates to novel substituted thiadiazolesulfonamides, processes for their preparation, and the use thereof as pharmaceuticals.

BACKGROUND OF THE INVENTION

The patents U.S. Pat. No. 4,758,578, U.S. Pat. No. 4,873,239 and U.S. Pat. No. 4,985,450 describe only those arylthiadiazolesulfonamides which are suitable for liberating sulfonamides unsubstituted on the nitrogen, and can therefore be used in particular for glaucoma treatment.

Some 1,2,4-thiadiazole-sulfonamide derivatives with a bactericidal action are known, for example, see N. M. Yousif et al., Egypt. J. Chem. 32 (1989) 607–614.

In efforts to develop more effective and better tolerated medicaments for treatment of rheumatic diseases, those compounds which are capable of influencing surplus or dysregulated cytokine production are gaining increasing importance. Annual Reports in Medicinal Chemistry volume 27, (1992), pages 209–218. Interleukin-Iβ (IL-1β) is to be noted in particular here as one of the most important pro-inflammatory cytokines. Its de novo synthesis takes place above all in the white blood cells and macrophages, where it must first be liberated from inactive pro-IL-1β in order to display its action. It plays a decisive role both in the control of the immune system and in inflammation processes, and thus has a causal relationship with the development of diseases, such as rheumatoid arthritis, arthrosis, various states of shock, or inflammatory bone diseases.

DETAILED DESCRIPTION OF THE INVENTION

According to the invention, it has now been found, surprisingly, that certain thiadiazolesulfonamides are potent inhibitors of cell interleukin-1β generation.

The invention relates to compounds of the formula (I):

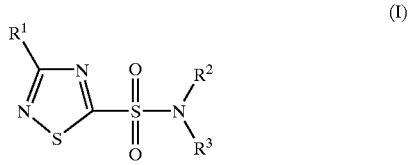

(I)

and/or a stereoisomeric form of compounds of the formula (I) and/or a physiologically tolerated salt of any of the forgoing in which:

$R^1$ is
1. phenyl,
2. phenyl which is mono- to trisubstituted by:
   2.1. —($C_1$–$C_6$)-alkyl, wherein alkyl is straight-chain, cyclic or branched,
   2.2. —OH,
   2.3. —O—C(O)—($C_1$–$C_6$)-alkyl-,
   2.4. —O—($C_1$–$C_6$)-alkyl,
   2.5. methylenedioxo,
   2.6. halogen,
   2.7. —$CF_3$,
   2.8. —CN,
   2.9. —$NO_2$,
   2.10. —C(O)—OH,
   2.11. —C(O)—O—($C_1$–$C_6$)-alkyl, or
   2.12. $R^3$—($R^4$)N—, wherein $R^3$ and $R^4$ are identical or different and are a hydrogen atom or ($C_1$–$C_6$)-alkyl, or
3. a heteroaromatic from the following group 3.1 to 3.15 (which is unsubstituted or substituted as described under 2.1 to 2.12):
   3.1. pyrrole,
   3.2. pyrazole,
   3.3. imidazole,
   3.4. triazole,
   3.5. thiophene,
   3.6. thiazole.
   3.7. oxazole,
   3.8. isoxazole,
   3.9. pyridine,
   3.10. pyrimidine,
   3.11. indole,
   3.12. benzothiophene,
   3.13. benzimidazole,
   3.14. benzoxazole, or
   3.15. benzothiazole;

$R^3$ is
1. a hydrogen atom or
2. ($C_1$–$C_6$)-alkyl;

$R^2$ is
1. ($C_1$–$C_7$)-alkyl, wherein alkyl is branched or unbranched and is unsubstituted or is mono- or disubstituted as described above under 2.1 to 2.12 or is substituted by a heteroalkyl ring or by a ($C_3$–$C_7$)-cycloalkyl, wherein the heteroalkyl ring or the ($C_3$–$C_7$)-cycloalkyl is unsubstituted or is mono- or disubstituted as described above under 2.1 to 2.12,
2. —($C_2$–$C_{10}$)-alkenyl, wherein alkenyl is straight-chain or branched,
3. ($C_3$–$C_7$)-cycloalkyl, wherein cycloalkyl is unsubstituted or is mono- or disubstituted as described above under 2.1 to 2.12,
4. phenyl, wherein phenyl is unsubstituted or mono- or disubstituted as described above under 2.1 to 2.12,
5. —$(CH_2)_m$-phenyl, wherein phenyl is unsubstituted or mono- or disubstituted as described above under 2.1 to 2.12, and m is the integer 1, 2, 3, 4, 5, or 6, or wherein one hydrogen atom of the —$(CH_2)_m$ radical is replaced by —OH,
6. —$(CH_2)_n$-heteroaryl, wherein heteroaryl is as defined under 3.1. to 3.15. and is unsubstituted or substituted as described above under 2.1 to 2.12, and n is the integer zero, 1, 2, 3, 4, 5, or 6,
7. —($C_2$–$C_6$)-alkyl-O—$R^6$, wherein $R^6$ is a hydrogen atom, benzyl, allyl, or ($C_1$–$C_6$)-alkyl, and wherein the alkyl radical is straight-chain or branched,
8. —($C_2$–$C_6$)-alkyl-C(O)—$OR^6$, wherein $R^6$ is as defined above,
9. —C($R^8$,$R^7$)—C(O)—X, wherein $R^8$ has the same meaning as $R^3$ above, $R^7$ is the radical of an α-amino acid, or $R^8$ and $R^7$ (together with the carbon atom to which they are bonded) form a 4- to 7-membered ring, and X is —OH, $NHR^6$ or —$OR^6$, wherein $R^6$ is as defined above, or 10. $R^2$ and $R^3$ (together with the nitrogen to which they are bonded) form a 4- to 7-membered ring, wherein at least one of the carbon atoms is optionally replaced by —O—, —S— or 11. —NH—, and wherein one, two or three of the carbon atoms in the ring are unsubstituted or mono- or disubstituted by
    10.1 $(C_1-C_2)$-alkyl,
    10.2 phenyl,
    10.3 —OH,
    10.4 =O,
    10.5 —C(O)—O—$(C_1-C_6)$-alkyl,
    10.6 —C(O)-phenyl, wherein phenyl is unsubstituted or substituted as described above under 2.1 to 2.12,
    10.7 —C(O)—$(C_1-C_6)$-alkyl, or
    10.8 —C—(O)—$OR^3$, wherein $R^3$ is a hydrogen atom or $(C_1-C_6)$-alkyl, and/or
    10.9 two carbon atoms in the ring form part of an additional phenyl radical, which is unsubstituted or substituted as described above under 2.1 to 2.12, or wherein the hydrogen atom in the —NH— optionally present is unsubstituted or is substituted by
    (a) $(C_1-C_3)$-alkyl,
    (b) —C(O)—$R^3$, wherein $R^3$ is as defined above,
    (c) —$(CH_2)_o$-phenyl, wherein phenyl is unsubstituted or mono- or disubstituted as described under 2.1 to 2.12, and o is the integer zero, one, or two,
    (d) benzoyl, which is unsubstituted or substituted as described above under 2.1 to 2.12, or
    (e) —C(O)—O—$(C_1-C_6)$-alkyl.

Currently preferred, are compounds of the formula (I) in which:
$R^1$ is phenyl which is unsubstituted or is monosubstituted by $(C_1-C_6)$-alkyl (wherein alkyl is straight-chain or branched), halogen, —O—$(C_1-C_3)$alkyl or —N—$R^3$—$(R^4)$, wherein $R^3$ and $R^4$ are identical or different and are a hydrogen atom or $(C_1-C_6)$-alkyl;
$R^3$ is a hydrogen atom or methyl;
$R^2$ is
1. $(C_1-C_4)$-alkyl, wherein alkyl is branched or unbranched and is unsubstituted or is monosubstituted as described under 2.1. to 2.12 or by phenyl, or is substituted by a heteroalkyl ring or by a $(C_3-C_7)$-cycloalkyl, wherein the heteroalkyl ring or the $(C_3-C_7)$-cycloalkyl is unsubstituted or is mono- or disubstituted as described under 2.1 to 2.12,
2. cyclohexyl,
3. —$C(R^8,R^7)$—C(O)—X, wherein $R^8$ is a hydrogen atom, $R^7$ is the radical of an α-amino acid, or $R^8$ and $R^7$ (together with the carbon atom to which they are bonded) form a 4- to 7-membered ring, and X is —OH or —$OR^6$, wherein $R^6$ is benzyl or $(C_1-C_3)$-alkyl, or
4. $R^2$ and $R^3$ (together with the nitrogen to which they are bonded) form a 4- to 7-membered ring, wherein one of the carbon atoms is optionally replaced by —O—, —S— or —NH—, and wherein one, two, or three of the carbon atoms in the ring are unsubstituted or are mono- or disubstituted by
    4.1 phenyl, which is unsubstituted or substituted by halogen,
    4.2 —OH,
    4.3 =O,
    4.4 —C(O)—OH,
    4.5 —C(O)—$(C_1-C_2)$-alkyl,
    4.6 $(C_1-C_3)$-alkyl, or
    4.7 —(O)—$OR^3$ and wherein $R^3$ is a hydrogen atom or $(C_1-C_6)$-alkyl, and optionally, two carbon atoms in the ring form part of an additional phenyl radical;
and optionally wherein the hydrogen atom in the —NH— optionally present in the ring is substituted by
    (a) $(C_1-C_3)$-alkyl,
    (b) —C(O)—$R^3$, wherein $R^3$ is a hydrogen atom or $(C_1-C_6)$-alkyl,
    (c) phenyl-$(CH_2)_o$—, wherein phenyl is unsubstituted or mono- or disubstituted as described under 2.1. to 2.12. and o is the integer zero, one or two, or
    (d) C(O)—O—$(C_1-C_3)$-alkyl.

Also currently preferred are compounds of the formula (I) in which:
$R^1$ is phenyl which is unsubstituted or is monosubstituted by $(C_1-C_3)$-alkyl (wherein alkyl is straight-chain or branched), chlorine, or —O-methyl;
$R^3$ is a hydrogen atom or methyl;
R is
1. $(C_1-C_4)$-alkyl (wherein alkyl is branched or unbranched and is unsubstituted or is monosubstituted by phenyl), C(O)—OH, halogen, piperidine or cyclohexyl (wherein piperidine or cyclohexyl is unsubstituted or is mono- or disubstituted by halogen or C(O)—OH),
2. cyclohexyl,
3. —$C(R^8,R^7)$—C(O)—X, wherein $R^8$ is a hydrogen atom, $R^7$ is methyl, and X is —OH or —OR, wherein R is benzyl or $(C_1-C_3)$-alkyl, or
4. $R^2$ and $R^3$ (together with the nitrogen to which they are bonded) form a morpholine-, piperidine-, piperazine- or tetrahydroisoquinoline-3-carboxylic acid radical, and wherein the carbon atoms in the ring are unsubstituted or are mono- or disubstituted by
    4.1 phenyl, which is substituted by chlorine or fluorine,
    4.2 methyl,
    4.3 =O,
    4.4 —C(O)—OH, or
    4.5 —C(O)-methyl;
and optionally wherein the hydrogen atom in the —NH— optionally present in the ring is substituted by
    (a) methyl,
    (b) —C(O)-methyl,
    (c) phenyl, which is substituted by chlorine, or
    (d) C(O)—O-ethyl.

The expression "$R^2$ and $R^3$ (together with the nitrogen to which they are bonded) form a 4- to 7-membered ring, wherein one of the carbon atoms is optionally replaced by —O—, —S— or —NH—" is understood as meaning radicals which are derived, for example, from azetidine, pyrroline, pyrrolidine, piperidine, piperazine, morpholine, thiomorpholine, tetrahydroisoquinoline, or tetrahydroisoquinoline-3-carboxylic acid (TIC). The expression "$R^8$ and R7 (together with the carbon to which they are bonded) form a 4- to 7-membered ring" is understood as meaning radicals which are derived, for example, from azetidine, pyrroline, pyrrolidine, piperidine, piperazine, morpholine, thiomorpholine, tetrahydroisoquinoline, or tetrahydro-isoquinoline-3-carboxylic acid (TIC).

The term "heteroalkyl ring" is understood as meaning radicals which are derived, for example, from piperidine, azetidine, pyrrolidine, isoxazolidine, morpholine, isothiazolidine, thiomorpholine, pyrazolidine, imidazolidine, piperazine, pyran, or thiopyran. The term "alkyl" or "alkenyl" is understood as meaning hydrocarbon radicals in which the carbon chain is straight-chain or branched. The alkenyl radicals can furthermore also contain two or more double bonds. Cyclic alkyl radicals are, for example, 3- to 7-membered monocyclic radicals, such as cyclopropyl, cyclobutyl, cyclopentyl, cyclohexyl, or cycloheptyl.

The term "halogen" is understood as meaning fluorine, chlorine, bromine, or iodine.

The expression "$R^7$ is the radical of an α-amino acid" is understood as meaning radicals R of the formula (II):

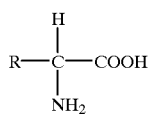

(II)

wherein R is derived from a natural or non-natural amino acid. Natural amino acid is understood as meaning glycine, alanine, valine, leucine, isoleucine, phenylalanine, tyrosine, tryptophan, serine, threonine, cysteine, methionine, asparagine, glutamine, lysine, histidine, arginine, glutamic acid, and aspartic acid.

Non-natural amino acid is understood as meaning those compounds of the formula (II) in which, for example, the radical R is modified by further substituents in the natural side chain, or R is a phenyl, cycloalkyl, such as cyclohexyl, or heteroaryl-$(CH_2)_n$, wherein heteroaryl is as defined under 3.1. to 3.15. and is unsubstituted or substituted as described above under 2.1 to 2.12, and n is the integer zero, 1, 2, 3, 4, 5, or 6.

Often employed, are the characteristic radicals of amino acids which are not naturally occurring, for example, 2-aminoadipic acid, 2-aminobutyric acid, 2-aminoisobutyric acid, 2,3-diaminopropionic acid, 2,4-diaminobutyric acid, 1,2,3,4-tetrahydroisoquinoline-1-carboxylic acid, 1,2,3,4-tetrahydro-isoquinoline-3-carboxylic acid, 2-aminopimelic acid, phenylglycine, 3-(2-thienyl)alanine 3-(3-thienyl) alanine, 2-(2-thienyl)glycine, 2-aminoheptanoic acid, pipecolinic acid, hydroxylysine, sarcosine, N-methylisoleucine, 6-N-methyllysine, N-methylvaline, norvaline, norleucine, ornithine, allo-isoleucine, allo-threonine, 4-hydroxyproline, 3-hydroxyproline, allo-hydroxylysine, 3-(2-naphthyl) alanine, 3-(1-naphthyl)alanine, homophenylalanine, homocysteine, homocysteine acid, homotryptophan, cysteine acid, 3-(2-pyridyl)alanine, 3-(3-pyridyl)alanine, 3-(4-pyridyl)alanine, phosphinothricin, 4-fluorophenylalanine, 3-fluorophenylalanine, 2-fluorophenylalanine, 4-chlorophenylalanine, 4-nitrophenylalanine, 4-aminophenylalanine, cyclohexylalanine, citrulline, 5-fluorotryptophan, 5-methoxytryptophan, methionine sulfone, methionine sulfoxide, or $NH_2$—NH—$CONH_2$, any of which are optionally further substituted. Of the natural or non-natural amino acids, both enantiomeric forms, the racemate, or any desired mixture are employed.

The invention furthermore relates to processes for the preparation of compounds of formula (I) and/or stereoisomeric forms compounds of formula (I) and/or physiologically tolerated salts of compounds of formula (I), which comprise:

(a) reacting an amine of the formula (III):

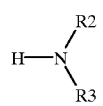

(III)

wherein $R^2$ and $R^3$ are as defined in formula (I), with a sulfonic acid derivative of the formula (IV):

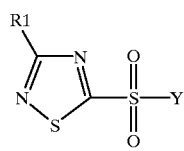

(IV)

wherein $R^1$ is as defined in formula (I) and Y is a halogen atom, imidazolyl, or —$OR^{10}$, wherein $R^{10}$ is a hydrogen atom, $(C_1–C_6)$-alkyl, phenyl, or benzyl,
in the presence of a base or optionally a dehydrating agent, to give a compound of the formula (I), or (b) converting 5-mercapto-thiadiazoles of the formula (V):

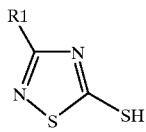

(V)

in which $R^1$ has the abovementioned meaning,
in the presence of sodium hypochlorite or chlorine and an amine of the formula (III) into a sulfenamine of the formula (VI):

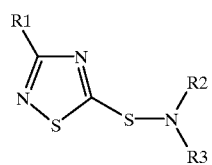

(VI)

in which $R^1$, $R^2$ and $R^3$ have the abovementioned meaning, and converting the compound of the formula (VI), in the presence of an oxidizing agent, such as per acids, in particular peracetic acid, or m-chloroperbenzoic acid, or hydrogen peroxide or potassium permanganate, into the compound of the formula (I); or (c) separating a compound of the formula (I) prepared by processes (a) or (b) which, because of its chemical structure, occurs in enantiomeric forms, into the pure enantiomers by salt formation with enantiomerically pure acids or bases, chromatography over chiral stationary phases or derivatization by means of chiral enantiomerically pure compounds, such as amino acids, separation of the diastereomers thus obtained and elimination of the chiral auxiliary groups; or (d) either isolating the compound of the formula (I) prepared by processes (a) or (b) in the free form or, in the case where acid or basic groups are present, converting it into physiologically tolerated salts.

The starting substances of the chemical reactions are known or can easily be prepared by methods known from the literature. Starting substances which are used for the preparation of a sulfonic acid derivative of the formula (IV), in particular if Y is a chlorine atom, are 5-mercaptothiadiazoles of the formula (V), which are usually oxidized directly to the corresponding sulfonic acid chlorides of the formula (IV) by passing chlorine into a suspension of the compound of the formula (V) in a mixture of acetic acid and water in a ratio of 1:2 to 5:1 at reaction temperatures of 0° C. to 30° C.

A compound of the formula (I) is prepared by process route (b) via the sulfenamides of the formula (VI), which are preferably formed from a 5-mercaptothiadiazole of the formula (V) and an amine of the formula (III) in an aqueous medium with sodium hypochlorite at reaction temperatures of −5° C. to 35° C. Per acids, such as peracetic acid or m-chloroperbenzoic acid, potassium permanganate or hydrogen peroxide are preferably employed for the subsequent oxidation to the compounds of the formula (I) (as described in U.S. Pat. No. 4,985,450, the disclosure of which is hereby incorporated by reference).

Physiologically tolerated salts are prepared from compounds of the formula (I) which are capable of salt formation, including stereoisomeric forms thereof, in a manner known in the art. Acids which may be present form stable alkali metal, alkaline earth metal, or optionally substituted ammonium salts with basic reagents, such as hydroxides, carbonates, bicarbonates, alcoholates, and ammonia, or organic bases, for example trimethyl- or triethylamine, ethanolamine, or triethanolamine, or else basic amino acids, for example lysine, ornithine, or arginine. If the compound of the formula (I) contains basic groups, stable acid addition salts can also be prepared with strong acids. Both inorganic and organic acids, such as hydrochloric, hydrobromic, sulfuric, phosphoric, methanesulfonic, benzenesulfonic, p-toluenesulfonic, 4-bromobenzene-sulfonic, cyclohexylamidosulfonic, trifluoromethylsulfonic, acetic, oxalic, tartaric, succinic, or trichloroacetic acid, are suitable.

The invention also relates to pharmaceuticals, which have an active content of at least one compound of the formula (I) and/or of a physiologically tolerated salt of the compound of the formula (I) and/or an optionally stereoisomeric form of the compound of the formula (I), together with a pharmaceutically suitable and physiologically tolerated excipient additive and/or other active compounds and auxiliaries.

IL-1β and its disease-causing actions are described in the patent specification U.S. Pat. No. 5,556,870, and in the literature cited therein, which are hereby incorporated by reference. On the basis of the pharmacological properties, the compounds according to the invention are suitable for the prophylaxis and treatment of diseases which are characterized by IL-1β and also those where IL-1β participates in their development, but in particular those where increased concentrations of IL-1 B participate in their course.

The diseases to be treated comprise, for example, leukemia, septic shock, hepatitis, HIV infections or musculoskeletal diseases, such as muscular degeneration, and degenerative joint diseases such as osteoarthrosis, spondylosis, chondrolysis following joint trauma or prolonged immobilization of joints following meniscus or patella injuries, or torn ligaments. These also include diseases of the connective tissue, such as collagenosis, periodontal diseases, or wound-healing disturbances. These further include chronic diseases of the locomotor system, such as inflammatory or immunologically or metabolism-related acute, and chronic arthritis, arthropathies, rheumatoid arthritis, myalgias or disturbances in bone metabolism.

The pharmaceuticals according to the invention are in general administered orally or parenterally. Rectal or transdermal administration is also possible.

The invention also relates to a process for the preparation of a pharmaceutical, which comprises bringing at least one compound of the formula (I) into a suitable presentation form with a pharmaceutically suitable and physiologically tolerated excipient and optionally further suitable active compounds, additives or auxiliaries.

Suitable solid or galenical formulation forms are, for example, granules, powders, coated tablets, tablets, microcapsules, suppositories, syrups, juices, suspensions, emulsions, drops, or injectable solutions, and preparations with protracted release of the active compound, for the preparation of which the customary auxiliaries, such as excipients, disintegrants, binders, coating agents, swelling agents, lubricants or slip agents, flavoring substances, sweeteners and solubilizers, are used. Frequently used auxiliaries which may be mentioned are magnesium carbonate, titanium dioxide, lactose, mannitol and other sugars, talc, milk protein, gelatin, starch, cellulose and its derivatives, animal and vegetable oils (such as cod-liver oil and sunflower, groundnut or sesame oil) polyethylene glycol, and solvents (such as, for example, sterile water and mono- or polyhydric alcohols, such as glycerol).

The pharmaceutical preparations are preferably prepared and administered in dosage units, each unit comprising a certain dose of the compound of the formula (I) according to the invention as the active constituent. In the case of solid dosage units, such as tablets, capsules, coated tablets or suppositories, this dose can be up to about 1000 mg, but is usually about 50 to 300 mg, and in the case of injection solutions in ampule form up to about 300 mg, but usually about 10 to 100 mg.

For the treatment of an adult patient weighing about 70 kg, daily doses of about 20 mg to 1000 mg of active compound, usually about 100 mg to 500 mg are indicated—depending on the activity of the compounds according to formula (I). Under certain circumstances, however, higher or lower daily doses may also be appropriate. The daily dose can be administered both by a single administration in the form of an individual dosage unit or a plurality of smaller dosage units and by multiple administrations of subdivided doses at certain intervals of time.

The $^1$H-NMR spectra were recorded on a 400 MHz apparatus from Bruker, as a rule with tetramethylsilane (TMS) as the internal standard and at room temperature (RT). DMSO-$d_6$ was used as the solvent in each case, unless noted otherwise. End products are as a rule determined by mass spectroscopy methods (FAB-, ESI-MS). Temperature data are in degrees Celsius and RT means room temperature (20° C. to 26° C.). The abbreviations used are either explained or correspond to the usual conventions.

Exemplary compounds within the scope of formula (I) are shown in the following Table 1.

TABLE 1

| Example Number | Compound of the formula | Comments | Melting point [° C.] | Mass M + 1 |
|---|---|---|---|---|
| 1 | | | 135–137 | |
| 2 | | | 114 | 312 |
| 3 | | | 146–147 | 352 |
| 4 | | | 108–109 | 332 |
| 5 | | | 135–136 | 324 |
| 6 | | | 155 | |

TABLE 1-continued

| Example Number | Compound of the formula | Comments | Melting point [° C.] | Mass M + 1 |
|---|---|---|---|---|
| 7 | Chiral (S-isomer structure) | S-isomer | 88–89 | 328 |
| 8 | (structure) | hydrochloride | 239-241 | |
| 9 | (structure) | | 194–195 | 382 |
| 10 | (structure) | | 196–198 | |
| 11 | (structure) | hydrochloride | 170-172 | |
| 12 | (structure) | | 129 | |
| 13 | (structure) | | 127–129 | |

TABLE 1-continued

| Example Number | Compound of the formula | Comments | Melting point [° C.] | Mass M + 1 |
|---|---|---|---|---|
| 14 | | | 202–203 | |
| 15 | | | 192–193 | |
| 16 | Chiral | S-isomer | 138–139 | |
| 17 | Chiral | S-isomer | 104–106 | |
| 18 | Chiral | S-isomer | 205 | |
| 19 | | | 222–224 | |

TABLE 1-continued

| Example Number | Compound of the formula | Comments | Melting point [° C.] | Mass M + 1 |
|---|---|---|---|---|
| 20 | | | 179 | |
| 21 | | | 183–185 | |
| 22 | Chiral | S-isomer | 133–134 | |
| 23 | Chiral | S-isomer | 92 | |
| 24 | | hydrochloride | 119-120 | |
| 25 | | | 169–170 | 359 |

TABLE 1-continued

| Example Number | Compound of the formula | Comments | Melting point [° C.] | Mass M + 1 |
|---|---|---|---|---|
| 26 | Chiral | R-isomer | 160–162 | 402 |
| 27 | | | | 397 |
| 28 | Chiral | S-isomer | 181–182 | 342 |
| 29 | Chiral | R-isomer | 142 | 314 |
| 30 | Chiral | S-isomer | 133–134 | 356 |
| 31 | | | 202–204 | 387 |

An exemplary method of making compounds within the scope of formula (I) is shown by the compound of example 16.

Example 16 (S)-2-(3-Phenyl-(1,2,4)-thiadiazole-5-sulfonylamino)propionic acid prepared by process variant (a)

A mixture of 0.72 g (5 mmol) of (S)-alanine tert-butyl ester and 0.86 g (7.5 mmol) of N-ethylmorpholine in 20 ml of toluene was added dropwise to a solution of 1.30 g (5 mmol) of 3-phenyl-(1,2,4)-thiadiazole-5-sulfonyl chloride in 20 ml of toluene at 0° C. in the course of 30 minutes, while stirring. After stirring the mixture for 2 hours, it was rendered acidic by addition of 100 ml of 1N hydrochloric acid, the organic phase was separated off, and the aqueous phase was extracted several times with toluene. Drying of the compound organic phases over sodium sulfate and concentration of the filtrate under reduced pressure gave an oily residue of the crude tert-butyl ester. To liberate the acid, the ester was taken up in 20 ml of methylene chloride and the mixture was treated with 3 ml of trifluoroacetic acid at RT for 4 hours. Thereafter, the mixture was concentrated to dryness under reduced pressure and the residue was recrystallized from toluene/methylcyclohexane (1:4).

Yield: 1.05 g of white needles (67% of theory)

Melting point: 138–139° C.

PHARMACOLOGY EXAMPLES

The actions of the compounds according to the invention on the release of IL-1β were demonstrated experimentally on an isolated blood cell fraction (mononuclear cells).

Pharmalogical Example I

The mononuclear cells were concentrated from freshly obtained human citrate blood by known standard processes. See, e.g., Tiku et al., J. Immunol. 136/10 (1986) 3677.

15 ml of Lymphoprep® (Molter GmbH, Heidelberg, FRG) was carefully introduced under a layer of 10 ml of freshly prepared human citrate blood and the mixture was then centrifuged at 400×g (Minifuge®, Heraeus, Hanau, FRG) at 20° C. for 40 minutes. The cell fraction, showing as a white ring in the phase boundary, was withdrawn with the aid of a syringe, diluted 1:1 (v/v) with PM-16 buffer (Serva, Heidelberg, FRG) and centrifuged again as above for 10 minutes. The supernatant was taken up in 10 ml of RPMI 1640 buffer (Gibco, Berlin, FRG), to which 300 mg/l of L-glutamine, 25 mmol/l of HEPES, 0.1 g/ml of streptomycin and 0.1 g/ml of penicillin had been added beforehand. The cell suspension, comprising about 90% lymphocytes and 10% monocytes, was adjusted to about 5 million cells/ml with the aid of a cell counter (type IT, Coulter Diagnostics, Krefeld, FRG). The cell viability was checked with the aid of the known lactate dehydrogenase method before and after the inhibition experiments. No change in the viability was found here.

The synthesis and release of cellular IL-1β was induced by adding a solution of 500 mg of lipopolysaccharide (Salmonella abortus equi, Sigma GmbH, Deisenhofen, FRG) in 0.01 ml of dimethyl sulfoxide/water (1:10, v/v) to 0.48 ml of the cell fraction described above. At the same time, a solution of the test substance in 0.01 ml was added to the cell fraction, and the mixture was left in a commercially available incubator at 37° C. for 20 hours. After the sample had been cooled to 0° C., it was centrifuged in a bench centrifuge for 1 minute and in each case 0.025 ml aliquots of the supernatant were investigated specifically for their IL-1β content with the aid of a commercially available "sandwich" enzyme immunoassay kit (Biosource, Ratingen, FRG), in accordance with the manufacturer's instructions. The control values, without addition of the test preparation, were determined and set at 100%. In particular, any influence of dimethyl sulfoxide on the IL-1β level was excluded by corresponding comparison measurements.

The dose-dependent IL-1β-inhibiting action of a compound of the formula (I) was demonstrated by determining the action potency thereof (complete inhibition of the release of IL-1β corresponds to 100% inhibition) at seven different concentrations. The concentration range was chosen here such that it comprised the ranges from 0% inhibition (that is to say without addition of the test substance) to at least 80% inhibition. The test substance concentration which led to 50% inhibition of the release of IL-1β was determined by extrapolation from the dose-effect relationship determined by graph or mathematically.

$IC_{50}$ value has been shown in Table 2 as micromoles/liter for the corresponding compounds of the formula (I) according to the invention.

TABLE 2

| Example Number | $IC_{50}$ [μM] | Example Number | $IC_{50}$ [μM] |
|---|---|---|---|
| 1 | 11 | 16 | 10 |
| 2 | 3 | 17 | 10 |
| 3 | 34 | 18 | 8 |
| 4 | 15 | 19 | 40 |
| 5 | 6 | 20 | 12 |
| 7 | 2 | 21 | 6 |
| 8 | 4 | 22 | 20 |
| 9 | 2 | 23 | 6 |
| 10 | 10 | 24 | 20 |
| 12 | 2 | 25 | 2 |
| 13 | 2 | | |
| 14 | 2 | | |
| 15 | 2 | | |

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and equivalency of the claims are to be embraced within their scope.

We claim:

1. A compound of formula (I):

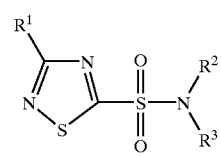

in any of its stereoisomeric forms, or in a mixture thereof in any ratio, or a physiologically tolerated salt of any of the foregoing, in which:

$R^1$ is 1. phenyl, 2. phenyl which is mono- to trisubstituted by:

2.1. —($C_1$–$C_6$)-alkyl, wherein alkyl is straight-chain, cyclic, or branched, 2.2. —OH, 2.3. —O—C(O)—($C_1$–$C_6$)-alkyl-,
2.4. —O—($C_1$–$C_6$)-alkyl,
2.5. methylenedioxo,
2.6. halogen,
2.7. —$CF_3$,
2.8. —CN,
2.9. —$NO_2$,
2.10. —C(O)—OH,
2.11. —C(O)—O—($C_1$–$C_6$)-alkyl, or
2.12. $R^3$—($R^4$)N—, wherein $R^3$ and $R^4$ are identical or different and are a hydrogen atom or ($C_1$–$C_6$)-alkyl, or
3. a heteroaromatic from the following group 3.1 to 3.15, which is unsubstituted or substituted as described under 2.1 to 2.12,
3.1. pyrrole,
3.2. pyrazole,
3.3. imidazole,
3.4. triazole,
3.5. thiophene,
3.6. thiazole,
3.7. oxazole,
3.8. isoxazole,
3.9. pyridine,
3.10. pyrimidine,
3.11. indole,
3.12 benzothiophene,
3.13. benzimidazole,
3.14. benzoxazole, or
3.15. benzothiazole;

$R^3$ is
1. a hydrogen atom or
2. —($C_1$–$C_6$)-alkyl;

$R^2$ is
1. —($C_1$–$C_7$)-alkyl, wherein alkyl is branched or unbranched and is mono- or disubstituted as described above under 2.2 to 2.12, or is substituted by a heteroalkyl ring or by a ($C_3$–$C_7$)-cycloalkyl, wherein the heteroalkyl ring or the ($C_3$–$C_7$)-cycloalkyl is unsubstituted or is mono- or disubstituted as described above under 2.1 to 2.12,
2. —($C_2$–$C_{10}$)-alkenyl, wherein alkenyl is straight-chain or branched,
3. —($C_3$–$C_7$)-cycloalkyl, wherein cycloalkyl is unsubstituted or is mono- or disubstituted as described above under 2.1 to 2.12,
4. phenyl, wherein phenyl is unsubstituted or mono- or disubstituted as described above under 2.1 to 2.12,
5 —($CH_2$)$_m$-phenyl, wherein phenyl is unsubstituted or mono- or disubstituted as described above under 2.1 to 2.12, and m is the integer 1, 2, 3, 4, 5, or 6, or wherein one hydrogen atom of the —($CH_2$)$_m$ radical is replaced by —OH,
6. —($CH_2$)$_n$-heteroaryl, wherein heteroaryl is as defined under 3.1 to 3.15, and is unsubstituted or substituted as described above under 2.1 to 2.12, and n is the integer zero, 1, 2, 3, 4, 5, or 6,
7. —($C_2$–$C_6$)-alkyl-O—$R^6$, wherein $R^6$ is a hydrogen atom, benzyl, allyl, or ($C_1$–$C_6$)-alkyl, and wherein the alkyl radical is straight chain or branched,
8. —($C_2$–$C_6$)-alkyl-C(O)—$OR^6$, wherein $R^6$ is as defined above,
9. —C($R^8$,$R^7$)—C(O)—X, wherein $R^8$ has the same meaning as $R^3$ above, $R^7$ is the radical of an α-amino acid, or $R^8$ and $R^7$ (together with the carbon atom to which they are bonded) form a 4- to 7-membered ring, and X is —OH, $NHR^6$, or —$OR^6$, wherein $R^6$ is as defined above, or
10. $R^2$ and $R^3$ (together with the nitrogen to which they are bonded) form a 4- to 7-membered ring, wherein at least one of the carbon atoms is optionally replaced by —O—, —S— or —NH—, and wherein one, two or three of the carbon atoms in the ring are unsubstituted or mono- or disubstituted by
10.1 ($C_1$–$C_2$)-alkyl,
10.2 phenyl,
10.3 —OH,
10.4 =O,
10.5 —C(O)—O—($C_1$–$C_6$)-alkyl,
10.6 —C(O)-phenyl, wherein phenyl is unsubstituted or substituted as described above under 2.1 to 2.12,
10.7 —C(O)—($C_1$–$C_6$)-alkyl, or
10.8 —C—(O)—$OR^3$, wherein $R^3$ is a hydrogen atom or ($C_1$–$C_6$)-alkyl, and optionally
10.9 two carbon atoms in the ring form part of an additional phenyl radical, which is unsubstituted or substituted as described above under 2.1 to 2.12, or
wherein the hydrogen atom in the —NH— optionally present is unsubstituted or is substituted by
(a) ($C_1$–$C_3$)-alkyl,
(b) —C(O)—$R^3$, wherein $R^3$ is as defined above,
(c) —($CH_2$)$_o$-phenyl, wherein phenyl is unsubstituted or mono- or disubstituted as described under 2.1 to 2.12, and o is the integer zero, one, or two,
(d) benzoyl, which is unsubstituted or substituted as described above under 2.1 to 2.12, or
(e) —C(O)—O—($C_1$–$C_6$)-alkyl;
provided that, when $R^1$ is phenyl and $R^2$ is phenyl, $R^3$ is other than hydrogen.

2. A compound as claimed in claim 1, wherein:
$R^1$ is phenyl which is unsubstituted or is monosubstituted by ($C_1$–$C_6$)-alkyl in which the alkyl is straight-chain or branched, halogen, —O—($C_1$–$C_3$)alkyl or —N—$R^3$—($R^4$), wherein $R^3$ and $R^4$ are identical or different and are a hydrogen atom or ($C_1$–$C_6$)-alkyl;
$R^3$ is a hydrogen atom or methyl;
$R^2$ is
1. ($C_1$–$C_4$)-alkyl, wherein alkyl is branched or unbranched, and is monosubstituted as described under 2.2 to 2.12 or by phenyl, or is substituted by a heteroalkyl ring or by a ($C_3$–$C_7$)-cycloalkyl, wherein the heteroalkyl ring or the ($C_3$–$C_7$)-cycloalkyl is unsubstituted or is mono- or disubstituted as described under 2.1 to 2.12,
2. cyclohexyl,
3. —C($R^8$,$R^7$)—C(O)—X, wherein $R^8$ is a hydrogen atom, $R^7$ is the radical of an α-amino acid, or $R^8$ and $R^7$ (together with the carbon atom to which they are bonded) form a 4- to 7-membered ring, and X is —OH or —$OR^6$, wherein $R^6$ is benzyl or ($C_1$–$C_3$)-alkyl, or
4. $R^2$ and $R^3$ (together with the nitrogen to which they are bonded) form a 4- to 7-membered ring, wherein one of the carbon atoms is optionally replaced by —O—, —S—, or —NH—, and wherein one, two, or three of the carbon atoms in the ring are unsubstituted or are mono- or disubstituted by
4.1 phenyl, which is unsubstituted or substituted by halogen,
4.2 —OH,
4.3 =O, 4.4 —C(O)—OH, 4.5 —C(O)—(C$_1$–C$_2$)-alkyl, 4.6 (C$_1$–C$_3$)-alkyl, or 4.7 —(O)—OR$^3$ and wherein R$^3$ is a hydrogen atom or (C$_1$–C$_6$)-alkyl.

3. A process for the preparation of a compound as claimed in claim 1 which comprises the steps of:

(a) converting a 5-mercapto-thiadiazole of the formula (V):

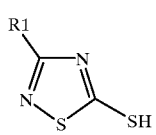

in which R$^1$ is as defined in claim 1, in the presence of sodium hypochlorite or chlorine, and an amine of the formula (III), into a sulfenamine of the formula (VI):

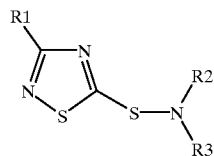

in which R$^1$, R$^2$, and R$^3$ are as defined in claim 1;

(b) converting the compound of the formula (VI), in the presence of an oxidizing agent, into one or more compounds of claim 1; and (c) isolating one or more of the compounds formed in the substantially free form, or converting the compound or compounds into physiologically tolerated salts.

4. The process of claim 3 wherein the oxidizing agent comprises at least one peracid.

5. The process of claim 4 wherein the oxidizing agent comprises peracetic acid or m-chloroperbenzoic acid or a mixture thereof.

6. The process of claim 4 wherein the oxidizing agent comprises hydrogen peroxide or potassium permanganate or a mixture thereof.

7. A process for the preparation of a compound as claimed in claim 3 further comprising the steps of separating one or more compounds formed into the substantially pure enantiomers by:

(a) salt formation with enantiomerically pure acids or bases;

(b) chromatography over chiral stationary phases; or (c) derivatization by means of chiral enantiomerically pure compounds, separation of the diastereomers thus obtained and elimination of the chiral auxiliary groups.

8. A process for the preparation of a compound as claimed in claim 3, wherein the chiral enantiometrically pure compounds are amino acids.

9. A composition of matter comprising at least one compound as claimed in claim 1 together with at least one additional additive chosen from pharmaceutically suitable and physiologically tolerated excipients, additives or auxiliaries.

10. A method of preparing a pharmaceutical composition comprising the steps of bringing at least one compound as claimed in claim 1 into a suitable presentation form with at least one pharmaceutically suitable and physiologically tolerated excipient, additive, or auxiliary.

* * * * *